United States Patent [19]

Ritter et al.

[11] 4,381,386

[45] Apr. 26, 1983

[54] POLYMERIZABLE ADHESIVES CONTAINING BORON INITIATORS

[75] Inventors: Wolfgang Ritter, Düsseldorf; Werner Gruber, Korschenbroich, both of Fed. Rep. of Germany

[73] Assignee: Henkel Kommanditgesellschaft auf Aktien, Düsseldorf-Holthausen, Fed. Rep. of Germany

[21] Appl. No.: 318,444

[22] Filed: Nov. 5, 1981

[30] Foreign Application Priority Data

Nov. 6, 1980 [DE] Fed. Rep. of Germany ....... 3041843

[51] Int. Cl.³ .................... C08F 30/06; C08F 130/06; C08F 230/06
[52] U.S. Cl. .................................. 526/239; 526/134; 526/196; 523/120; 427/236; 427/407.1; 427/331; 156/327
[58] Field of Search ....................... 526/134, 239, 196; 523/120

[56] References Cited

U.S. PATENT DOCUMENTS 3,130,185  4/1964  Welch ................................ 260/88.7

Primary Examiner—Joseph L. Schofer
Assistant Examiner—Bernard Lipman
Attorney, Agent, or Firm—Hammond & Littell, Weissenberger and Muserlian

[57] ABSTRACT

Polymerizable adhesives mixtures containing ethylenic double bonds capable of polymerizing and boron compounds as polymerization initiators, wherein the boron compounds are organoboron compounds and contain at least one boron-carbon bond or one boron-hydrogen bond and have practically no spontaneous combustibility in air. The adhesives harden after a short time to give stable adhesive bonds, even in the presence of moisture.

6 Claims, No Drawings

POLYMERIZABLE ADHESIVES CONTAINING BORON INITIATORS

BACKGROUND OF THE INVENTION

The invention concerns two-component adhesives based on compounds containing ethylenic double bonds that are mixed with certain organoboron compounds as initiators, which can be handled in air and do not ignite spontaneously.

Adhesives that harden by polymerization of compounds containing ethylenic double bonds have been known for a long time. These can be prepared from methacrylic acid esters or acrylic acid esters of various alcohols with the addition of peroxides or hydroperoxides, as initiators, and additional adjuvants. Besides these, adhesive agents and filling agents are known for dental medical or surgical uses that contain as an essential component trialkyl boron compounds, such as triethylboron, tri-n-butylboron, etc., in addition to acrylates or methacrylates and other reaction partners containing ethylenic double bonds. Such trialkyl boron compounds, however, have the disadvantage that they are readily flammable so that the handling of these adhesives causes considerable difficulties. An attempt to correct this problem has been made in that one can react the trialkyl boron compounds with 0.3 to 0.9 mols of oxygen. In addition, trialkyl boron compounds were also reacted with amines to reduce the spontaneous combustion. With these steps, the ignition temperture is shifted within a range of from 0° to 75° C., but a considerable uncertainty remains in the handling of such mixtures. In particular, they are not suitable for construction bonding.

OBJECTS OF THE INVENTION

An object of the present invention is the development of a reaction adhesive, that is, a two-component adhesive, that can be handled safely and results in good bonds at a practicable pot life, even with the binding of materials that cannot be dried.

An additional object of the invention is the development of adhesives that can be used safely as adhesives in the area of dental medicine and as bonding and gluing agents in surgery.

A further object of the invention is the development of reaction adhesives that can be used on metal surfaces and are suitable for the bonding of bones or teeth or other hard, living tissue.

A yet further object of the present invention is the development of a reaction adhesive consisting essentially of a polymerizable system containing polymerizable ethylenic double bonds and an organoboron compound to initiate polymerization. This organoboron compound contains at least one boron-carbon bond or one boron-hydrogen bond and has practically no spontaneous combustibility in air.

These and other objects of the invention will become more apparent as the description thereof proceeds.

DESCRIPTION OF THE INVENTION

The drawback of the prior art have been overcome and the above objects have been achieved with the discovery of reaction adhesives, that is, a two-component adhesive, based on polymerizable systems containing ethylenic double bonds as well as certain boron compounds as polymerization initiators. The new reaction adhesives are characterized by the fact that an organoboron compound containing a boron-carbon bond or a boron-hydrogen bond is used, which possesses practically no spontaneous combustibility in air. Suitable organoboron compounds should have a stability comparable to that of sodium borohydride and lithium aluminum hydride and thus can be handled in a similar manner.

More particularly, the present invention relates to a reaction adhesive consisting essentially of a polymerizable system containing polymerizable ethylenic double bonds and an amount suffucient to initiate polymerization of an organoboron compound containing at least one boron-carbon bond or one boron-hydrogen bond and having practically no spontaneous combustibility in air.

Suitable initiators for the new systems are preferably to be selected from the following groups of boron compounds:

(a) Boron compounds with sterically hindering groups of the general formulae:

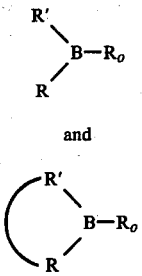

in which R' or R separately or together represents an aliphatic monocycle or dicycle with 3 to 25 carbon atoms, and $R_o$ stands either for H or a, if desired, linear or cyclic or branched hydrocarbon radical with 3 to 15 carbon atoms;

(b) Boron compounds that are reaction products of aromatic dihydroxy compounds with $BH_3$ or their alkylation products, with the general formula

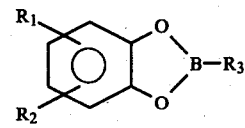

in which $R_1$, $R_2$ and $R_3$ represent either H or an alkyl radical with 1 to 4 carbon atoms, and $R_1$ and $R_2$ together may also stand for an aromatic hydrocarbon ring and/or an aliphatic hydrocarbon cycle having from 3 to 15 carbon atoms, and (c) Boron compounds of the general formula:

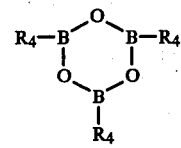

in which $R_4$ represents a linear or branched alkyl radical with 1 to 6 carbon atoms.

Consequently, numerous known boron alkyls, or those that can be prepared by a known method, are suitable as the organoboron compounds. Typical representatives of these organoboron compounds are, for example:
9-borabicyclo-(3,3,1)-nonane,
diisopinocampheylborane,
dicyclohexylborane,
2,3-dimethyl-2-butylborane (=thexylborane)
3,5-dimethylborinane, and
diisoamylborane.

Among these compounds, the first-mentioned 9-borabicyclo-(3,3,1)-nonane is preferred for practical reasons. The compounds mentioned above can be prepared, for example, from sodium borohydride and borontrifluoride with suitable olefines or diolefins. Diborane or its ether, amine or sulfide complexes may also be used for the preparation.

A compilation of the possible methods of preparation of suitable organoboron compounds is found in the monograph by Herbert C. Brown, 1975, "Organic Synthesis via Boranes," John Wiley & Sons. Hydroborating products of dialkyl boranes and olefines also may be used as initiators. Useful as olefines are alkenes and cycloalkenes having from 3 to 25 carbon atoms, such as butene, isobutene, hexene, cyclohexene; vinyl chloride; allyl chloride; allylamine or also methylmethacrylate, vinyl acetate or methyl crotonate.

Among the suitable organoboron compounds worth mentioning are, for example:
diisopinocampheylbutyl boron,
thexylcyclohexylcyclopentyl boron,
thexyllimonyl boron,
trinorbornyl boron,
B-butyl-9-borabicyclo-(3,3,1)-nonane,
B-isobutyl-9-borabicyclo-(3,3,1)-nonane,
B-[2-(4-cyclohexenyl)-ethyl]-9-borabicyclo-(3,3,1)-nonane,
B-cyclopropyl-9-borabicyclo-(3,3,1)-nonane,
B-p-tolyl-9-borabicyclo-(3,3,1)-nonane, and
B-tert.-butyl-3,5-dimethylborinane.

Also suitable are reaction products of 1,2-dihydroxybenzenes, such as pyrocatechol with boron hydride (catechol borane), the formula of group (b) above where $R_1$ and $R_2$ are hydrogen and $R_3$ is hydrogen, and tri-n-butyl boroxine, the formula of group (c) above where $R_4$ is n-butyl. The initiators may be added purely or in mixtures with solvents and polymers to get suitable viscosities for further processing.

The initiators to be used are added in amounts of about 0.1% to about 10% based on the portion of the polymerizable system that can be polymerized. About 0.5% to about 3%, calculated on the added monomers, are preferably used. The initial preparation of a preadduct from the initiator with an ethylenically unsaturated monomer may be advantageous.

Suitable as polymerizable components of the reaction adhesive according to the invention are numerous compounds that contain the ethylenic double bonds, for example, the (meth)acrylic acid esters [where (meth)acrylic designates methacrylic and acrylic] of monohydric alcohols, preferably alkanols having from 1 to 12 carbon atoms, thus methyl (meth)acrylate, ethyl-(meth)acrylate, butyl (meth)-acrylate, acrylate, and ethylhexyl (meth)acrylate, the (meth)acrylic acid esters of polyhydric alcohols, preferably alkanepolyols having from 2 to 12 carbon atoms and from 2 to 6 hydroxyl groups and ethers thereof as, for example, ethylene glycol, diethylene glycol, polyethylene glycol and trimethylol propane, the di- and mono-(meth)acrylates of glycerol, the di(meth)acrylates of triethylene glycol and tetraethylene glycol and of dipropylene glycol, tripropylene glycol, tetrapropylene glycol and pentapropylene glycol, the di(meth)acrylates of ethoxylated or propoxylated diphenylol propane.

Also suitable are (meth)acrylic acid esters of alcohols that are derived from dihydroxymethyltricyclododecane or also those that have been prepared from tricyclodecane, with two alcoholic groups in the ring system having been extended by reaction with dicarboxylic acids, such as maleic acid or also cyclohexanedicarboxylic acid or terephthalic acid. Further suitable are reaction products of epoxides (propylene oxide, ethylene oxide) with diphenylol propane, for example. Also suitable are the (meth)acrylic acid esters obtainable by the reaction of diisocyanates with hydroxyalkyl (meth)acrylates.

Finally, other polymerizable compounds can be added to the new systems, preferably in small amounts, such as vinyl acetate, alkyl crotonates and mono- and dialkyl maleates, styrene, divinylbenzene and other similar substances.

Also suitable are 2-acryloyloxyethyl phosphate, 2-methacryloyloxyethyl phosphate, bis-2-acryloyloxyethyl phosphate, bis-2-methacryloyloxyethyl phosphate, tris-2-acryloxyethyl phosphate, tris-2-methacryloyloxyethyl phosphate and acid amides such as dimethylene-bis-(meth)-acrylamide, tetramethylene-bis-(meth)acrylamide, tri(meth)-acryloyldiethylenetriamine and other similar substances.

Furthermore, it is frequently advantageous to add polymerizates, such as polymethyl methacrylate, polyvinyl acetate, chlorosulfonated polypropylene, polyurethanes or similar substances as strengtheners and simultaneously as thickeners, to make the processing of the adhesives easier.

The further addition of additives, such as fillers, for example, powdered quartz or similar substances, is of advantage in many cases. The coloring with suitable dyes can also be advantageous in some cases.

The new adhesives are characterized by the fact that they possess a high curing rate at room temperature and show good adhesive strength with a large number of different surfaces after a relatively short time. To be especially emphasized is the fact that a quick and good adhesion is obtained also on moist surfaces. Thus the adhesives can be used as so-called construction adhesives for the bonding of metals, wood, glass, ceramics and plastics. Furthermore, they are suitable as adhesive agents and filling agents in dental medicine. They are also suitable for the bonding or gluing or hard tissue, especially bones or also teeth. It is to be understood that metal surfaces can be bonded to bones or teeth or similar hard tissue with the reaction adhesive of the invention.

The following examples are illustrative of the invention without being limiting thereto.

EXAMPLE 1

4 Grams of polymethyl methacrylate (commerical powder, glass temperature 180° C.) were dissolved with stirring in a beaker in 4.5 gm of methyl methacrylate and 0.5 gm of methacrylic acid. With continued more intensive stirring, 0.3 gm of 9-borabicyclo-(3,3,1)-nonane was added.

The mixture had a pot life of about 5 minutes. Beeachwood test pieces adhered together were used to determine the average tensile and shear strength of the adhesive bond after 24 hours. A value of 15 N/mm$^2$ (DIN 68 602) was obtained. Furthermore, sandblasted and degreased sheet iron was used to measure the tensile and shear strength of the adhesive bond, also after 24 hours. A value of 24 N/mm2 (DIN 53 281/3) was obtained.

EXAMPLES 2 TO 5

In these reaction adhesive mixtures, 0.3 gm of 9-borabicyclo-(3,3,1)-nonane was used as an initiator, and 4 gm of polymethyl methacrylate was used as a thickener, respectively. To these were added different monomers and adhesive bonds were made with beechwood and iron test pieces. The amounts of monomer used and the pot life are compiled for each example under its respective number in Table 1 below. These are followed by the average values determined for the tensile and shear strength after 24 hours with iron and beechwood.

TABLE 1

| Example | Grams | Monomer | Pot Life Min. | Tensile and Shear Strength N/mm$^2$ Fe | Wood |
|---|---|---|---|---|---|
| 2 | 4.5 | Methyl methacrylate | 15 | 15 | 8 |
| 3 | 4.5 | Methylmethacrylate | 25 | 15 | 8 |
|   | 0.5 | Ethylene glycol dimethacrylate | | | |
| 4 | 3.0 | Methyl methacrylate | 20 | 15 | 9 |
|   | 0.5 | Ethylene glycol dimethacrylate | | | |
|   | 1.5 | Butyl acrylate | | | |
| 5 | 4.5 | Methyl methacrylate | 20 | 18 | 11 |
|   | 0.5 | Ethylene glycol mono-methacrylate | | | |

PREPARATION OF THE INITIATOR

Under the exclusion of oxygen, 12 gm of 9-borabicyclo-(3,3,1)-nonane were dissolved in 100 ml of anhydrous and degassed tetrahydrofuran. This solution was reacted with 8.6 gm of degassed methyl methacrylate, with the continued exclusion of oxygen. An exothermic reaction was observed during the dropwise addition. After the generation of heat had subsided, the excess tetrahydrofuran was removed under vacuum. The initiator obtained in this manner is used in the following examples.

EXAMPLE 6

0.5 Gram of the initiator prepared as above was added to a solution of 4 gm of polymethyl methacrylate in 4.5 gm of methyl methacrylate and 0.5 gm of methacrylic acid, and after the addition of 0.35 gm of methyl benzoate, mixed well.

Test pieces of beechwood were bonded together with this reaction adhesive and the tensile and shear strength was determined after 24 hours. It was 13 N/mm2 (DIN 68 602) on the average.

Sand-blasted and degreased test pieces of iron were also glued together, and the tensile and shear strength was determined after a 24-hour waiting period. It was 25 N/mm2 (DIN 53 281/3) on the average.

EXAMPLE 7

The following were mixed intensively and quickly: 3 gm of chlorosulfonated polypropylene (1.7% S; 1.85% Cl), 6.2 gm of methyl methacrylate and 0.8 gm of methacrylic acid, as well as 0.5 gm of the initiator described above. Also added was 0.35 gm of methyl benzoate. Test pieces of beechwood and iron were treated corresponding to the procedure described in DIN 68 602 and DIN 53 281/3 and glued together.

The average tensile and shear strengths were determined: beechwood 10 N/mm2 and iron 27 N/mm2.

EXAMPLE 8

Freshly extracted human molars were boiled for 4 minutes in 3% by weight of $H_2O_2$, to remove pieces of tissue. For fixation, the teeth were glued with the roots into beechwood blocks, using a commerical two-component adhesive based on unpolymerized methyl methacrylate. The crowns of the teeth were face-ground. The cut surface consisted of tooth enamel and to a lesser degree of dentin. This was first degreased with trichloroethylene, then brushed with an aqueous solution of 50% aqueous phosphoric acid and then with hydroxyethyl methacrylate and wiped with cellulose after 5 minutes. Two test pieces each were glued together with the reaction adhesive mixture described in Example 1, applying light pressure, and torn apart after 24 hours, under tensile conditions. The hardening was carried out: (a) in the air, (b) in water at 37° C..

The tearing was performed after 24 hours. The recorded tensile strengths are the means of six measurements each: (a) 6.4 N/mm2, (b) 6.8 N mm2.

EXAMPLE 9

Human teeth were glued by the method described in Example 8, using an adhesive of 4.5 gm of methyl methacrylate, 0.5 gm of hydroxyethyl methacrylic acid, 4 gm of polymethyl methyacrylate and 0.3 gm of 9-borabicyclo-(3,3,1)-nonane, and the following tensile strengths were determined after 24 hours:

(a) in the air, (b) in water at 37° C.
(a) 8.3 N/mm2, (b) 5.1 N/mm2.

EXAMPLE 10

The adhesive mixture of Example 7 was used to glue human teeth as described in Example 8, and the following tensile strengths were determined after 24 hours:

(a) in the air, (b) in water at 37° C.
(a) 5.1 N/mm2, (b) 5.1 N/mm2.

EXAMPLE 11

As described in Example 1, an adhesive mixture was prepared from 40 gm of methyl methacrylate, 10 gm of ethylene glycol dimethacrylate, 10 gm of bis-2-methacryloxyethyl phosphate, 50 gm of polymethyl methacrylate and 1.8 gm of 9-borabicyclo-(3,3,1)-nonane, and human teeth were glued analogous to Example 8. The following tensile strengths were determined after 24 hours:

(a) in the air, (b) in water at 37° C.
(a) 10.3 N/mm2, (b) 11.3 N/mm2.

EXAMPLE 12

Degreased, tissue-free Kompacta pieces (from the outer layer of a long bone from the calf) measuring 6×0.8×0.6 cm (Kieler bone chip) were glued without further pretreatment on the 0.6×0.8 cm surfaces applying slight pressure and using the adhesive from Example 11. Hardening was performed: (a) in the air, (b) in water at 37° C..

The tearing was carried out after 24 hours. The recorded tensile strengths are averages of six measurements each: (a) 11 N/mm2, (b) 10.5 N/mm2.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A two-component reaction adhesive consisting essentially of a polymerizable system hardenable at room temperature and containing polymerizable ethylenic double bonds and an amont sufficient to initiate polymerization of an organoboron compound with sterically hindering groups and containing at least one boron-carbon bond or one boron-hydrogen bond and having practically no spontaneous combustibility in air and having the formula:

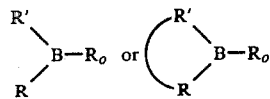

wherein R' and R, separately or together, represent an aliphatic monocycle or dicycle with 3 to 25 carbon atoms and $R_o$ is selected from the group consisting of hydrogen and linear or branched or cyclic hydrocarbon having from 3 to 15 carbon atoms.

2. The reaction adhesive of claim 1 wherein said amount sufficient to initiate polymerization is from 0.1% to 10% by weight, based on the total amount of the polymerizable portion.

3. The reaction adhesive of claim 1 wherein said organoboron compound is pre-adducted with an ethylenically unsaturated monomer.

4. The reaction adhesive of claim 2 wherein said organoboron compound is pre-adducted with an ethylenically unsaturated monomer.

5. The reaction adhesive of claim 1 wherein said organoboron compound is 9-borabicyclo-(3,3,1)-nonane.

6. The reaction adhesive of claim 3 wherein said organoboron compound is 9-borabicyclo-(3,3,1)-nonane.

* * * * *